United States Patent [19]

Inoue

[11] Patent Number: 4,594,459
[45] Date of Patent: Jun. 10, 1986

[54] PREPARATION OF P-ISOPROPENYL PHENOL AND RELATED COMPOUNDS

[75] Inventor: Kimio Inoue, Midland, Mich.

[73] Assignee: The Dow Chemical Company, Midland, Mich.

[21] Appl. No.: 715,550

[22] Filed: Mar. 25, 1985

[51] Int. Cl.⁴ .................. C07C 37/52; C07C 39/06
[52] U.S. Cl. ............................ 568/781; 568/705; 568/706
[58] Field of Search ................. 568/781, 806, 805

[56] References Cited

U.S. PATENT DOCUMENTS

| | | | |
|---|---|---|---|
| 2,497,503 | 2/1950 | Jones | 568/806 |
| 3,969,196 | 7/1976 | Zosel | 203/49 |
| 4,028,220 | 7/1977 | Urquhart | 208/8 |
| 4,054,611 | 10/1977 | Mimaki et al. | 568/781 |
| 4,108,760 | 8/1978 | Williams et al. | 208/11 |
| 4,124,528 | 11/1978 | Modell | 568/781 |
| 4,131,749 | 12/1978 | Kiedik et al. | 568/806 |
| 4,147,624 | 4/1979 | Modell | 210/32 |
| 4,153,063 | 5/1979 | Roselius et al. | 131/143 |
| 4,242,528 | 12/1980 | Kato et al. | 568/781 |
| 4,245,128 | 1/1981 | Kato et al. | 568/806 |
| 4,247,570 | 1/1981 | Zosel | 426/481 |
| 4,251,559 | 2/1981 | Margolis et al. | 426/490 |
| 4,258,221 | 3/1981 | Knudsen et al. | 568/806 |
| 4,345,976 | 8/1982 | Peter et al. | 203/49 |
| 4,351,966 | 9/1982 | Flock | 568/806 |

FOREIGN PATENT DOCUMENTS

| | | | |
|---|---|---|---|
| 1144343 | 12/1979 | Canada | 203/8 |
| 29849 | 12/1969 | Japan | 568/806 |
| 669074 | 3/1952 | United Kingdom | 568/806 |
| 8188434 | 8/1959 | United Kingdom | 568/806 |
| 880895 | 10/1961 | United Kingdom | 568/806 |
| 903062 | 8/1962 | United Kingdom | 568/806 |
| 905994 | 9/1962 | United Kingdom | 568/806 |

OTHER PUBLICATIONS

Chemical Abstract 23:4429a, Shering-Kahlbaum.
Chemical Abstract 58:476d, Bayer.
Chemical Abstract 60:7936g, Smolin et al.
Chemical Abstract 68:59280y, Krimm et al.
Chemical Abstract 69:67031d, Aliev et al.
Chemical Abstract 70:48600w, Kahoves.
Chemical Abstract 83:96727e.
Chemical Abstract 92:128562b.
Chemical Abstract 92:163698x.
Chemical Abstract 92:215059m.
Chemical Abstract 92:215060e.
CHemical Abstract 94:156528e.
Chemical Abstract 95:97366w, Mimaki.

*Primary Examiner*—Werren B. Lone
*Attorney, Agent, or Firm*—Paul D. Hayhurst

[57] ABSTRACT

Prepare p-isopropenyl phenol and other alkenyl aromatic compounds by contacting a dihydroxydiphenyl alkane or a related substituted diaromatic alkane with an alkaline catalyst and at least one gas under supercritical conditions such that p-isopropenyl phenol or the corresponding related alkenyl aromatic compound is produced.

20 Claims, No Drawings

PREPARATION OF P-ISOPROPENYL PHENOL AND RELATED COMPOUNDS

BACKGROUND OF THE INVENTION

This invention relates to a process for producing alkenyl aromatic compounds. More particularly, it relates to a process for cleaving certain diphenyl alkanes.

It is well-known that dihydroxydiphenyl alkanes can be cleaved by heating them in the presence of an alkaline catalyst to give phenol and alkenyl phenols, and several methods have been proposed for this cleavage reaction. Unfortunately, the alkenyl phenol coproduct is prone to oligomerization or polymerization under the reaction conditions. This is particularly true of p-isopropenyl phenol. Polymerization of the alkenyl phenol undesirably results in reduced yield of the desired alkenyl phenol, and requires further product purification steps to obtain the alkenyl phenol. While the dimers can be "cracked back" to the desired monomer, this requires further processing and additional expense.

An example of a prior art process is taught in U.S. Pat. No. 4,245,128, which describes a process for cleaving a dihydroxydiphenyl alkane to produce an alkenyl phenol and a polymer thereof by continuously feeding the dihydroxydiphenyl alkane into an inert organic solvent containing certain basic catalysts, heating the resulting mixture at a temperature between 150° C. and 250° C. at from 10 to 100 mm Hg and maintaining the concentration of the dihydroxydiphenyl alkane in the reaction medium at not more than 30 percent by weight to cleave the dihydroxydiphenyl alkane, and continuously distilling the cleavage products out of the reaction system. Said process typically produces the dimer of p-isopropenyl phenol in amounts greater than or equal to the amount of p-isopropenyl phenol produced.

Extraction using gases under supercritical conditions has been used to separate many diverse substances. For example, U.S. Pat. No. 4,247,570 and 4,251,559 describe the use of supercritical gas extractants in the decaffeination of coffee. Additionally, supercritical gas extraction has been used to remove nicotine from tobacco (U.S. Pat. No. 4,153,063), to treat hydrocarbons, including coal (U.S. Pat. No. 4,028,220) and tar sands (U.S. Pat. No. 4,108,760), and to separate isotopes of chlorine (CA 1,144,343). U.S. Pat. No. 3,969,196 discloses a method of separation which employs a supercritical gas extractant. Said method is limited to a temperature range in which the quantity of organic compound taken up by the gas phase varies inversely with the temperature. U.S. Pat. No. 4,345,976 discloses a process for separating substances of low volatility. Said process is limited in that it requires an entrainer in addition to the supercritical gas.

In view of the deficiencies of the prior art, it would be desirable to have a process for the selective preparation of p-isopropenyl phenol and related alkenyl aromatic compounds which could produce mainly the desired monomers to the virtual exclusion of dimers, polymers, etc.

SUMMARY OF THE INVENTION

The process of the present invention is such a monomer-selective process. The process involves contacting a dihydroxydiphenyl alkane or a related cleavable organic compound with an alkaline catalyst using gases under supercritical conditions such that p-isopropenyl phenol or the corresponding related alkenyl hydroxyaromatic compound is produced. Surprisingly, the process of the present invention can produce monomers selectively without producing large quantities of dimers, trimers, and polymers.

DETAILED DESCRIPTION OF THE INVENTION

The cleavable organic materials suitable for use in the process of the present invention include substituted aromatic compounds having an optionally substituted aliphatic bridging moiety containing from 2 to about 7 carbon atoms. The cleavable organic compound contains at least one electron-withdrawing or electron-donating moiety as a substituent on at least one of the aromatic moieties of the compound. Preferred organic compounds suitable for cleavage are represented generally by the formula:

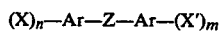

wherein each Ar independently is an aromatic moiety, Z is an optionally substituted aliphatic moiety having from 2 to about 7 carbon atoms, X and X' are independently electron-withdrawing or electron-donating moieties, and n and m are integers, with the proviso that the quantity (m+n) is greater than zero. Typical examples of X and X' include —R, —OR, —NRR', halo, —NO$_2$, —SO$_3$R and —COOR, wherein R and R' are independently hydrogen, alkyl, aralkyl or aryl, with the proviso that all occurrences of X and X' cannot be hydrogen. Preferably, X and X' are —OH and each Ar is phenyl. More preferred compounds are represented by the formula:

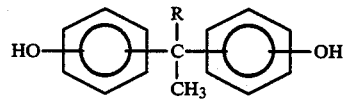

wherein R preferably is hydrogen or alkyl of 1 to about 3 carbon atoms. Most preferably, R is methyl, and the hydroxyl groups are in the para positions, i.e., 2,2-bis(4-hydroxyphenyl)propane is the most preferred organic compound to be cleaved. Examples of typical cleavable organic compounds include 2,4'-(1-methylethylidene)-bis(phenol) and 1,1-bis(4-hydroxyphenyl)cyclohexane. Additional examples are listed in U.S. Pat. No. 4,245,128; and the teachings of said patent relating to cleavable organic aromatic compounds are incorporated herein by reference.

The process of the present invention basically involves a loading step, a removal step, and a release step. The loading step involves contacting the starting organic compound with a gas under supercritical conditions such that the starting organic compound is cleaved. The removal step involves removing the gas, including and dissolved, dispersed or entrained compounds, from the mixture after the gas passes through the mixture. The release step involves separating the gas from all or part of the compounds which were taken up by the gas.

The critical temperature of a gas is well-known to physical chemists as the temperature above which the gas cannot be liquefied regardless of the pressure to which it is subjected. The pressure necessary to liquefy the gas at its critical temperature is the critical pressure. The process of the present invention typically employs as an extractant a gas or gas mixture at a temperature above the critical temperature and at a pressure at or above the critical pressure, i.e., the gas is in a supercritical condition. For the purposes of the present invention, the term "supercritical condition(s)" includes those conditions which are "near-supercritical", i.e., those coniditions of temperature and pressure which approach the supercritical state. Typically, near-supercritical conditions include reduced temperatures, $T_r$, which are greater than about 0.9 and reduced pressures, $P_r$, which are greater than about 0.5. "Reduced pressure", or $P_r$, is defined as the ratio of the process pressure to the critical pressure of the gas being employed, i.e., $P_r = P/P_c$, wherein $P_c$ is the critical pressure of the gas employed, and P is the process pressure. Similarly, "reduced temperature", or $T_r$, is defined as $T_r = T/T_c$, wherein T is the process temperature and $T_c$ is the critical temperature of the gas employed.

A variety of gases and gas mixtures may be used as the gas which is under supercritical conditions and which serves as an extraction agent. Several guides should be used in the selection of an appropriate gas. Advantageously, the critical temperature of the gas is lower than the temperature at which the process is to be carried out. Preferably, the critical temperature of the gas is near the process temperature. The critical temperature must also not be so low that cooling to subcritical conditions is difficult for standard industrial equipment. For these reasons, the critical temperature of the gas chosen will generally be between about 10° C. and about 300° C. Gases having a relatively low critical pressure (e.g., about 30–50 atmospheres; this group includes, e.g., hydrocarbons, halogenated hydrocarbons, alkylamines, ether, etc.) are preferred, generally speaking, to gases having higher critical pressures (above 50 atmospheres). In special cases, however, e.g., on grounds of safety or because of a particular specific interaction between the gas present in a supercritical state and the substance(s) to be present in the reactor, gases having a high critical pressure may also be used as the supercritical agent. The gas should not be reactive with any of the materials to be present in the reactor.

Some typical gases suitable for extractions, along with their critical temperatures and pressures are as follows:

| Gas | $T_c$ (°C.) | $P_c$ (atm) |
| --- | --- | --- |
| Carbon dioxide | 31.0 | 72.9 |
| Ethane | 32.2 | 48.2 |
| Propane | 96.7 | 42.0 |
| $CHF_3$ | 25.9 | 46.9 |
| $N_2O$ | 36.5 | 71.7 |
| $CClF_3$ | 28.9 | 38.2 |
| $C_2H_2F_2$ | 30.1 | 43.8 |
| $CHClF_2$ | 96.0 | 48.5 |
| Ethene | 9.9 | 51.2 |
| Propene | 91.9 | 45.4 |

Propene and propane are preferred in the preparation of p-isopropenyl phenol.

For additional examples of gases which may be used in supercritical gas extraction processes, see U.S. Pat. No. 4,345,976, the teachings of which, with respect to the gases which may be used in supercritical gas extraction processes, are incorporated herein by reference.

Generally, it is preferred to operate the process of the present invention without an entrainer. However, if desired, a suitable entrainer can be employed to improve the absorbability and selectivity of the gaseous extraction agent with respect to certain materials. The entrainer need not be under supercritical conditions. Water and benzene are examples of typical entrainers.

In the present process, the material to be extracted is contained in an apparatus suitable for withstanding high temperature and pressure, such as an autoclave. In the loading step, gas under supercritical conditions is supplied to an extraction vessel and is allowed to thoroughly contact the material to be extracted. Preferably, the gas will be supplied and removed continuously. The loading step can be conducted at a temperature which is below or above the melting point of the cleavable organic material. The reduced pressure, $P_r$, in the extraction vessel during the loading step preferably is from about 0.8 to about 5.

In the removal step, at least part of the supercritical gas phase which had been contacted with the reaction mixture is removed, typically while remaining under supercritical conditions, from the extraction vessel. The removed gas phase is the feed stream for the release step.

In the release step, the gas removed from the extraction vessel is brought to a new thermodynamic state, usually by changing temperature or pressure or both. The gas in its new state partially or completely loses its capacity to absorb the extracted components, which will separate from the gas and are recoverable. The gas can then be recycled to the extraction vessel. Preferably, the solute is separated from the supercritical gas solvent by reducing the system pressure. For reasons of cost, energy conservation, and convenience, it is preferred to keep the change in pressure as small as possible while obtaining the separation of solvent and solute. More preferably, the solute is separated from the supercritical solvent by changing the temperature of the system. The temperature change can be an increase or a decrease in temperature, depending upon the operating conditions in the extraction cell. Typically, the temperature is decreased to achieve separation. The decision to achieve the separation by raising or lowering the temperature is guided by the knowledge that separation is achieved by decreasing the solubility of the solute compounds in the supercritical gas. The solubility is a function of the density of the supercritical gas solvent, and is a function of the vapor pressure of the solute at a given set of conditions. Generally speaking, separation is achieved at lower pressures by a temperature increase, while at higher pressures it is achieved by a temperature decrease. For any given set of operating conditions, the separation conditions can be easily determined by experimentation. Additionally, separation of the solute from the supercritical gas solvent can be accomplished using known separation techniques such as adsorption, absorption, distillation, crystallization, and the like.

The solubility of a solute in a supercritical fluid is dependent on solute/solvent interactions. These interactions determine the solvent power of the supercritical fluid for the particular solute. They are dependent on the nature of the solute and solvent and on the density of the supercritical solvent. In general, as the density of the supercritical solvent increases at constant temperature, its solvent power and solute solubility increase. Solubility is also dependent on solute vapor pressure. The higher the vapor pressure the higher the solubility of the solute in the supercritical fluid. Increasing temperature increases solute vapor pressure and at the same time decreases the supercritical solvent density. These are competing effects and because of this the dependence of solute solubility on temperature is somewhat complex. Solute solubility may increase, decrease, or remain relatively constant with increasing temperature. The effect of temperature changes depends on whether solvent density or solute vapor pressure is dominant. At high pressures solvent density is relatively independent of temperature and in general solute vapor pressure dominates and solubility increases with increasing temperature. At pressures near the critical pressure solvent density is relatively sensitive to temperature and in general solvent density dominates and solubility decreases with increasing temperature. At intermediate pressures the two effects may balance and solubility remain relatively constant with increasing temperature.

A particular material will be subjected to the extraction process for a period of time which may be minutes or hours. The material may be supplied to an extraction vessel continuously or it may be supplied in batches. After the extraction period, the material is removed from the autoclave and separated from any absorbed gas which can then be returned to circulation. The particularly desired isomer may be contained in this raffinate phase, or in the gas phase, depending on the properties of the isomers which are being extracted.

As with other methods of separation, a plurality of extraction systems may be set up in a series to further enrich the desired isomer in the raffinate or in the extract. In that case, the starting material for the second and subsequent extraction stages will be either the material recovered from the gas phase of the previous extraction or the material recovered from the raffinate phase of the previous extraction or both.

The alkaline catalyst employed in the process of the present invention can be essentially any alkaline material which catalyzes the cleavage reaction. A catalytic amount of the catalyst is employed. Typically, from about 0.5 to about 5 percent by weight of the alkaline catalyst is employed based on the weight of the starting hydroxyaromatic compound employed. Suitable alkaline catalysts are well-known, and include, for example, oxides, hydroxides or carbonates of alkali metals or alkaline earth metals, such as sodium hydroxide, potassium hydroxide, sodium carbonate, potassium carbonate, magnesium oxide, calcium oxide and calcium hydroxide; alkali metal salts of phenols, such as sodium phenoxide, or a sodium salt of a condensation product formed between phenol or cresol and acetone (e.g., bisphenol A); and alkali metal salts of weakly acidic fatty acids such as sodium acetate. The preferred catalyst is magnesium oxide modified with potassium hydroxide, i.e. a catalyst comprising magnesium oxide and potassium hydroxide. See, e.g., Preparation 1.

When a cleavable organic compound is subjected to gases under supercritical conditions in the presence of an alkaline catalyst according to the process of the present invention, the monomeric cleavage products can be recovered with little or no dimers or polymers. Typically, the products contain less than about 1 weight percent of dimers of isopropenyl phenol, preferably, less than about 0.5 weight percent, based on the weight of the cleavage products. Most preferably, no dimer is produced as detected by liquid chromatographic means. Should any dimer be produced, it can be recycled to the reactor feed stream. Normally this recycle will be unnecessary using the process of the present invention.

SPECIFIC EMBODIMENTS

The following preparation and examples are provided for illustrative purposes only and are not intended to limit the scope of the invention or claims. All parts and percentages are by weight unless otherwise specified.

Preparation 1

Preparation of Modified Magnesium Oxide Catalyst

One mole of alkali metal hydroxide (66 g of 85 weight percent KOH, the remaining 15 weight percent being water) is mixed with enough water to make a 1000 ml solution. This solution is added at room temperature to 500 g of MAGOX Premium Grade magnesium oxide (available from Basic Chemicals Division of Basic, Inc.), and the resulting mixture is stirred for approximately one hour to obtain a smooth paste. The reaction is exothermic. The paste is filtered in a Buchner funnel, and is not washed. The filter cake is transferred to glass trays and is spread to a thickness of approximately ½ inch. The glass trays containing the ½ inch thick cake are placed in an air circulating oven for about 2 hours at about 110° C. to dry the cake. The dried cake is ground and is stored for later use.

EXAMPLE 1

The starting material is 11.9 g of a mixture consisting of 87.1 percent 2,2-bis(4-hydroxyphenyl) propane (p,p'-isopropylidenediphenol), 6.5 percent 2-(4-hydroxyphenyl)-2-(2-hydroxyphenyl) propane (o,p'-isopropylidenediphenol), and 6.4 percent other organic compounds. The mixture of starting materials and 0.10 g of the modified catalyst of Preparation 1 are fed to a tubular reactor (pipe bomb) in an air bath. The reactor is equipped with peripheral equipment which is typical of that employed in processes which are conducted under supercritical conditions. The reactor is heated to a temperature of 227° C. Then, propane is liquefied and pumped to an operating pressure of 825 psia (5.67 MPa) and is then heated to the operating temperature. Supercritical propane is introduced to the mixture of starting materials and dissolves p-isopropenyl phenol and phenol as they form. The propane flow rate is approximately 0.03 g propane/g initial starting material/minute. The following loadings are obtained for the first 8 aliquots of propane.

TABLE I

| Aliquot Number | g propane | Loadings (mg product/g propane) | |
|---|---|---|---|
| | | phenol | p-isopropenyl phenol |
| 1 | 12.4 | 11.7 | 7.7 |
| 2 | 14.5 | 10.6 | 8.4 |
| 3 | 10.4 | 9.8 | 8.5 |
| 4 | 14.5 | 9.1 | 8.6 |
| 5 | 15.5 | 9.4 | 9.7 |
| 6 | 15.5 | 8.2 | 8.9 |
| 7 | 15.5 | 8.4 | 9.5 |
| 8 | 15.5 | 7.6 | 9.2 |

The pressure and temperature of the supercritical propane which contains dissolved p-isopropenyl phenol and phenol then are decreased from the operating conditions to ambient pressure and temperature across a micro-metering valve. The decrease in pressure and temperature, i.e., a decrease in propane density, causes a dramatic decrease in solvent power, and all dissolved materials condense out and are collected. The amount of propane which flows through the reactor is measured using a wet test meter.

After passing 670 g of propane through the starting materials, a total of 2.75 g and 5.08 g, respectively, of phenol and p-isopropenyl phenol are collected. The conversion of the starting materials is 92.3 percent, and the yields of phenol and p-isopropenyl phenol are respectively 64.7 percent and 84.0 percent. Liquid chromatographic analysis indicates that less than 0.5 percent dimerized isopropenyl phenol is detected in the product.

EXAMPLE 2

The starting material is 12.9 g of a mixture consisting of 93.1 percent 2,2-bis(4-hydroxyphenyl) propane, 3.1 percent 2-(4-hydroxyphenyl)-2-(2-hydroxyphenyl)propane and 3.8 percent other organic compounds. The mixture of starting materials and 0.12 g of the modified catalyst of Preparation 1 are fed to a reactor and are decomposed as in Example 1. The reaction conditions used in this example were propene at 227° C. and 775 psia (5.34 MPa). The propene flow rate is approximately 0.05 g propene/g initial starting material/minute. The following loadings are obtained for the first 10 aliquots of propene.

TABLE II

| Aliquot Number | g propene | Loadings (mg product/g propane) | |
|---|---|---|---|
| | | phenol | p-isopropenyl phenol |
| 1 | 7.7 | 25.5 | 5.8 |
| 2 | 9.9 | 30.7 | 7.9 |
| 3 | 9.9 | 29.5 | 9.6 |
| 4 | 14.8 | 23.4 | 9.5 |
| 5 | 14.8 | 20.0 | 10.8 |
| 6 | 14.8 | 16.5 | 11.2 |
| 7 | 14.8 | 13.9 | 11.5 |
| 8 | 14.8 | 12.0 | 11.4 |
| 9 | 14.8 | 11.0 | 12.4 |
| 10 | 15.1 | 9.5 | 12.8 |

After passing 430 g of propene through the starting materials, a total of 3.22 g and 3.85 g, respectively, of phenol and p-isopropenyl phenol are collected. The conversion of the starting materials is 97.8 percent, and the yields of phenol and p-isopropenyl phenol are respectively 64.3 percent and 54.0 percent. Liquid chromatographic analysis indicates that less than 0.4 percent dimerized isopropenyl phenol is detected in the product.

What is claimed is:

1. A process for the cleavage of cleavable organic compounds, comprising contacting a cleavable organic compound represented by the formula $$(X)_n-Ar-Z-Ar-(X')_m$$

wherein each Ar independently is an aromatic moiety, Z is an optionally substituted aliphatic moiety having from 2 to about 7 carbon atoms, X and X' are independently electron-withdrawing or electron-donating moieties, and n and m are integers, with the proviso that the quantity (m+n) is greater than zero; with an alkaline catalyst and at least one gas under supercritical conditions such that the corresponding monomeric alkenyl aromatic compound is produced.

2. The process of claim 1 wherein X and X' are identical.
3. The process of claim 1 wherein X and X' are selected from the group —OR and —NRR'.
4. The process of claim 1 wherein each Ar is a single aromatic ring.
5. The process of claim 1 wherein the Ar moieties have 6 carbon atoms each and wherein X and X' are in the 4 and 4' positions of the respective aromatic rings.
6. The process of claim 2 wherein the cleavable compound is represented by the formula

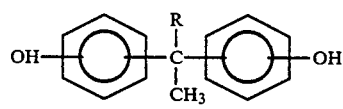

wherein R preferably is hydrogen or alkyl of 1 to about 3 carbon atoms.

7. The process of claim 6 wherein R is alkyl of 1 to about 3 carbon atoms.
8. The process of claim 7 wherein R is methyl.
9. The process of claim 2 wherein n and m are 1.
10. A process of claim 1 for the cleavage of cleavable organic compounds, comprising:
(a) contacting an alkaline catalyst and at least one cleavable organic compound with a compressed gas under supercritical conditions such that the gas selectively takes up at least one monomeric cleavage product;
(b) separating the gas, including any of the mixture taken up by the gas in step (a), from the mixture not taken up by the gas in step (a); and
(c) separating at least part of the mixture taken up by the gas from the gas in order to recover at least one monomeric cleavage product.
11. The process of claim 10 wherein the supercritical gas is propene.
12. The process of claim 10 wherein the supercritical gas is propane.
13. A process for the preparation of p-isopropenyl phenol, comprising contacting p-isopropylidenediphenol with an alkaline catalyst and at least one gas under supercritical conditions such that p-isopropenyl phenol is produced.
14. The process of claim 13 wherein less than about one weight percent of dimers of p-isopropenyl phenol is detectable in the product stream using liquid chromatographic means.
15. The process of claim 14 wherein less than about 0.5 weight percent of dimers of p-isopropenyl phenol is detectable.
16. The process of claim 13 wherein the supercritical gas is propene.
17. The process of claim 13 wherein the supercritical gas is propane.
18. The process of claim 13 wherein the catalyst comprises an alkali metal or alkaline earth metal.
19. The process of claim 18 wherein the catalyst comprises magnesium oxide and potassium hydroxide.
20. A process of claim 1 wherein the catalyst comprises magnesium oxide and potassium hydroxide.

* * * * *

UNITED STATES PATENT AND TRADEMARK OFFICE
CERTIFICATE OF CORRECTION

PATENT NO.    :   4,594,459
DATED         :   June 10, 1986
INVENTOR(S)   :   Kimio Inoue It is certified that error appears in the above-identified patent and that said Letters Patent is hereby corrected as shown below:

Cover page under OTHER PUBLICATIONS, first line,
"Chemical Abstract 23:4429a" should read
-- Chemical Abstract 23:4229a --.

Column 3, line 7, "coniditions" should read -- conditions --.

Column 7, line 29, in the heading for TABLE II, first line,
"propane" should read -- propene --.

Column 8, line 12, first line of Claim 6, "2" should read
-- 1 --.

Column 8, line 26, Claim 9, "2" should read -- 1 --.

Signed and Sealed this

Twenty-fourth Day of February, 1987

Attest:

DONALD J. QUIGG

Attesting Officer     Commissioner of Patents and Trademarks